US009415213B2

(12) United States Patent
Venook et al.

(10) Patent No.: US 9,415,213 B2
(45) Date of Patent: Aug. 16, 2016

(54) SYSTEMS AND LEADS FOR IMPROVED RF COMPATIBILITY AND METHODS OF MANUFACTURE AND USE

(71) Applicant: BOSTON SCIENTIFIC NEUROMODULATION CORPORATION, Valencia, CA (US)

(72) Inventors: Ross Daniel Venook, Millbrae, CA (US); Matthew Lee McDonald, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 209 days.

(21) Appl. No.: 14/073,603

(22) Filed: Nov. 6, 2013

(65) Prior Publication Data

US 2014/0135614 A1  May 15, 2014

Related U.S. Application Data

(60) Provisional application No. 61/725,904, filed on Nov. 13, 2012.

(51) Int. Cl.
*A61N 1/37* (2006.01)
*A61N 1/08* (2006.01)
*A61N 1/05* (2006.01)
*A61B 5/055* (2006.01)

(52) U.S. Cl.
CPC ............... *A61N 1/08* (2013.01); *A61N 1/0551* (2013.01); *A61B 5/055* (2013.01); *A61N 2001/086* (2013.01)

(58) Field of Classification Search
CPC ..................... A61N 2001/086; A61N 1/14
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |

(Continued)

OTHER PUBLICATIONS

Rezai, A. R., et al., "Neurostimulation system used for deep brain stimulation (DBS): MR safety issues and implications of failing to follow guidelines." Investigative Radiology, 39:300-303; 2004.

(Continued)

*Primary Examiner* — Edward Moran
*Assistant Examiner* — Natasha Patel
(74) *Attorney, Agent, or Firm* — Lowe Graham Jones PLLC; Bruce E. Black

(57) ABSTRACT

An implantable electrical stimulation lead includes a lead body having a distal end, a proximal end, and a longitudinal length; a plurality of electrodes disposed along the distal end of the lead body; a plurality of terminals disposed along the proximal end of the lead body; and a plurality of conductors electrically coupling the plurality of electrodes to the plurality of terminals. To reduce or redistribute current induced in the conductors during an MRI procedure, an internal conductive structure, such as a dummy coil or hollow metal tube, or non-therapeutic electrodes may be provided. Alternatively or additionally, a multi-layer region of the conductors may extend beneath the electrodes or terminals or the electrodes or terminals may vary in size or surface area.

11 Claims, 9 Drawing Sheets

(56) References Cited

U.S. PATENT DOCUMENTS

| | | | |
|---|---|---|---|
| 7,672,734 B2 | 3/2010 | Anderson et al. | |
| 7,761,165 B1 | 7/2010 | He et al. | |
| 7,949,395 B2 | 5/2011 | Kuzma | |
| 7,974,706 B2 | 7/2011 | Moffitt et al. | |
| 8,175,710 B2 | 5/2012 | He | |
| 8,224,450 B2 | 7/2012 | Brase | |
| 8,322,026 B2 | 12/2012 | McDonald | |
| 8,335,570 B2 | 12/2012 | McDonald | |
| 8,340,782 B2 | 12/2012 | McDonald et al. | |
| 8,364,278 B2 | 1/2013 | Pianca et al. | |
| 8,364,279 B2 | 1/2013 | McDonald et al. | |
| 8,380,324 B2 | 2/2013 | McDonald et al. | |
| 8,478,423 B2 | 7/2013 | McDonald et al. | |
| 2001/0014820 A1* | 8/2001 | Gielen | A61N 1/0529 607/116 |
| 2005/0070972 A1* | 3/2005 | Wahlstrand | A61N 1/05 607/48 |
| 2007/0150036 A1 | 6/2007 | Anderson | |
| 2009/0171421 A1* | 7/2009 | Atalar | A61N 1/056 607/63 |
| 2009/0259272 A1* | 10/2009 | Reddy | A61N 1/0573 607/28 |
| 2010/0057175 A1* | 3/2010 | McDonald | A61B 5/0422 607/116 |
| 2012/0041528 A1* | 2/2012 | Mehdizadeh | A61N 1/056 607/115 |
| 2012/0158072 A1 | 6/2012 | Venook et al. | |
| 2012/0191167 A1 | 7/2012 | McDonald et al. | |

OTHER PUBLICATIONS

Nyenhuis, J. A., et al., "MRI and implanted medical devices: basic interactions with an emphasis on heating." IEEE Transactions on Device and Materials Reliability, 5:467-478; 2005.

* cited by examiner

SYSTEMS AND LEADS FOR IMPROVED RF COMPATIBILITY AND METHODS OF MANUFACTURE AND USE

CROSS-REFERENCE TO RELATED APPLICATIONS

This application claims the benefit under 35 U.S.C. §119 (e) of U.S. Provisional Patent Application Ser. No. 61/725,904 filed on Nov. 13, 2012, which is incorporated herein by reference.

FIELD

The present invention is directed to the area of implantable electrical stimulation systems and methods of making and using the systems. The present invention is also directed to implantable electrical stimulation leads having a dummy coil or other arrangement to reduce electrode heating as a result of exposure to a RF field, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

One embodiment is an implantable electrical stimulation lead including a lead body having a distal end, a proximal end, and a longitudinal length; a plurality of electrodes disposed along the distal end of the lead body; a plurality of terminals disposed along the proximal end of the lead body; a plurality of conductors electrically coupling the plurality of electrodes to the plurality of terminals; and at least one internal conductive structure disposed within the distal end or proximal end of the lead body near at least one of the electrodes or terminals, respectively. The at least one internal conductive structure is not conductively connected to the electrodes, terminals, or conductors. Examples of internal conductive structures include, but are not limited to, a dummy coil, a hollow tube, or two conductive elements coupled together by a conductive wire.

Another embodiment is an implantable electrical stimulation lead including a lead body having a distal end, a proximal end, and a longitudinal length; a plurality of therapeutic electrodes disposed along the distal end of the lead body; a plurality of terminals disposed along the proximal end of the lead body; a plurality of conductors electrically coupling the plurality of therapeutic electrodes to the plurality of terminals; and at least one non-therapeutic electrode disposed along the distal end of the lead body. The at least one non-therapeutic electrode is not conductively connected to the therapeutic electrodes, terminals, or conductors.

Yet another embodiment is an implantable electrical stimulation lead including a lead body having a distal end, a proximal end, and a longitudinal length; a plurality of electrodes disposed along the distal end of the lead body; a plurality of terminals disposed along the proximal end of the lead body; and a plurality of conductors electrically coupling the plurality of electrodes to the plurality of terminals. The electrodes are differently sized, patterned, or have different surface areas to make more uniform an amount of induced current dissipated through each of the electrodes in response to an MRI procedure.

A further embodiment is an implantable electrical stimulation lead including a lead body having a distal end, a proximal end, and a longitudinal length; a plurality of electrodes disposed along the distal end of the lead body; a plurality of terminals disposed along the proximal end of the lead body; and a plurality of conductors electrically coupling the plurality of electrodes to the plurality of terminals. The plurality of conductors includes a first conductor and the first conductor including a unit. The unit includes a first conductor segment extending along the lead body from a beginning point to a first position, a second conductor segment extending along the lead body from the first position to a second position, and a third conductor segment extending along the lead body from the second position to an endpoint. The first position is between the second position and the endpoint, and the second position is between the beginning point and the first position. The first, second, and third conductor segments are arranged so as to form at least one single-layer region formed from at least a portion of a single one of the first, second, or third conductor segments and a multi-layer region formed from overlapping portions of at least two of the first, second, or third conductor segments. The multi-layer region extends beneath at least two of the plurality of electrodes.

Another embodiment is an electrical stimulation system including any of the leads described above; a control module configured and arranged to electrically couple to the proximal end of the lead body; and a connector for receiving the lead, the connector having a proximal end, a distal end, and a longitudinal length. The control module includes a housing, and an electronic subassembly disposed in the housing. The connector includes a connector housing defining a port at the distal end of the connector, the port configured and arranged for receiving the proximal end of the lead body, and a plurality of connector contacts disposed in the connector housing, the connector contacts configured and arranged to couple to at least one of the plurality of terminals disposed on the proximal end of the lead body.

A further embodiment is a method for stimulating tissue that includes implanting any of the leads described above into tissue a patient such that at least some of the electrodes are disposed in proximity to tissue to be stimulated; and providing current to at least some of the electrodes from an electrically coupled pulse generator.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having a dummy coil or other arrangement to reduce electrode heating as a result of exposure to a RF field, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; 7,244,150; 7,672,734; 7,761,165; 7,949,395; 7,974,706; 8,175,710; and 8,364,278; and U.S. Patent Application Publication No. 2007/0150036, all of which are incorporated by reference.

Figure 1:
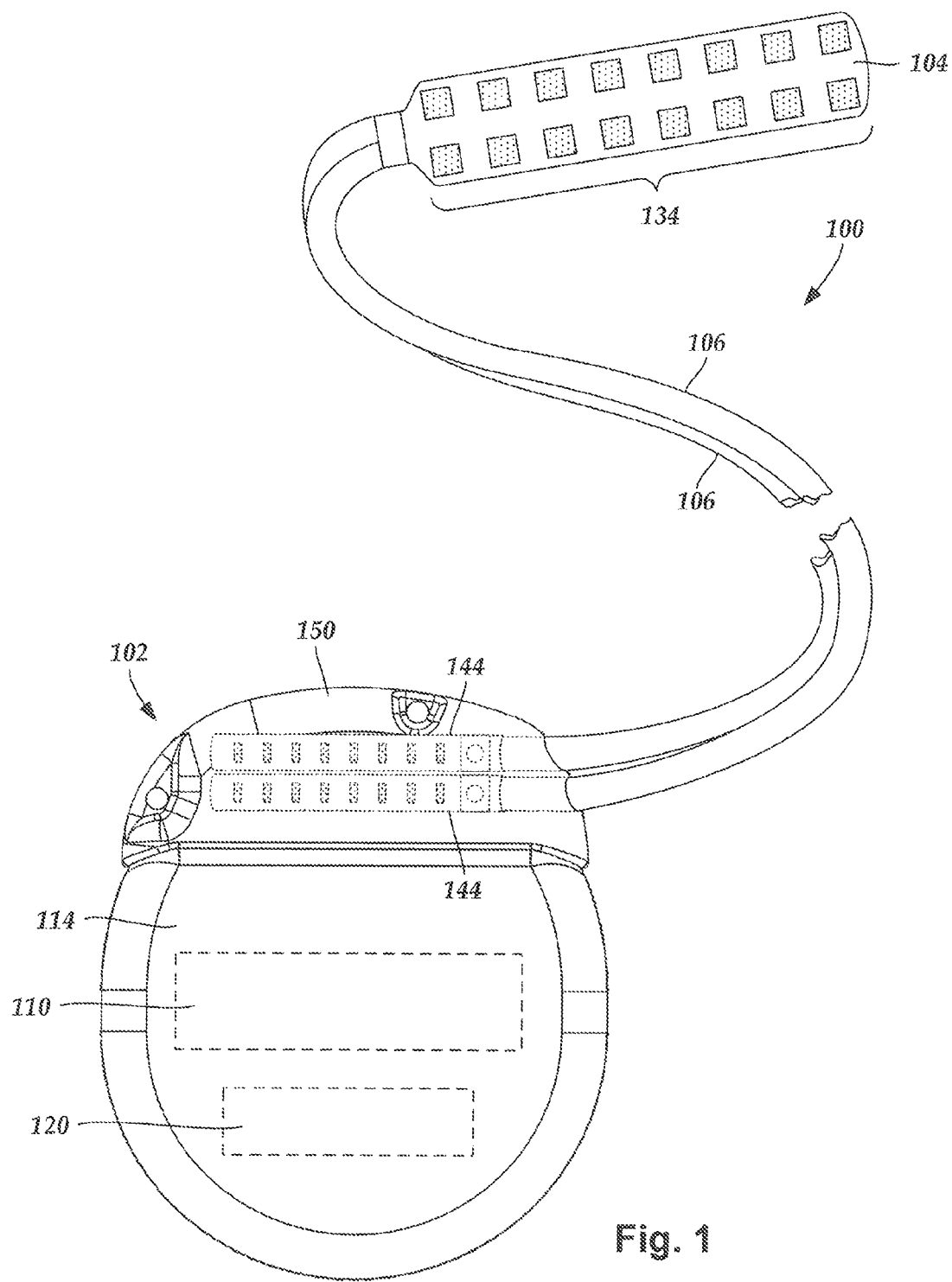
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIGS. 3A-3B; and 340 of FIG. 3C) disposed in the connector assembly 144 and terminals (e.g., 310 in FIGS. 3A-3C) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
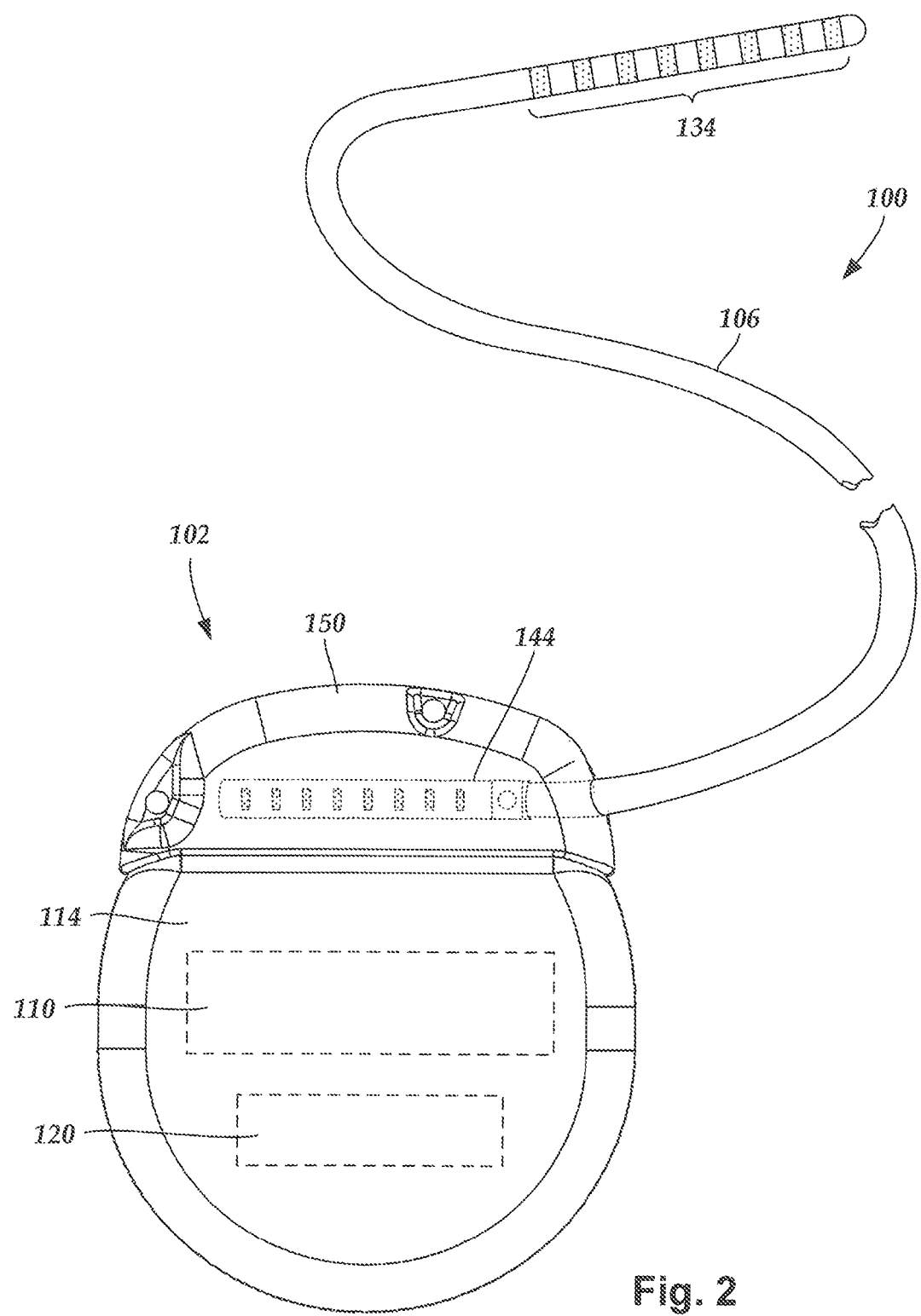
FIG. 2 is a schematic view of another embodiment of an electrical stimulation system that includes a percutaneous lead body coupled to the control module of FIG. 1, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead body 106.

The electrical stimulation system or components of the electrical stimulation system, including one or more of the lead bodies 106, the control module 102, and, in the case of a paddle lead, the paddle body 104 are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A-3C) are typically disposed at the proximal end of the one or more lead bodies 106 for connection to corresponding conductive contacts (e.g., 316 in FIGS. 3A-3B; and 340 of FIG. 3C) in connector assemblies (e.g., 144 in FIGS. 1-3C) disposed on, for example, the control module 102 (or to other devices, such as conductive contacts on a lead extension, an operating room cable, a splitter, an adaptor, or the like).

Conductive wires (not shown) extend from the terminals (e.g., 310 in FIGS. 3A-3C) to the electrodes 134. Typically, one or more electrodes 134 are electrically coupled to a terminal (e.g., 310 in FIGS. 3A-3C). In some embodiments, each terminal (e.g., 310 in FIGS. 3A-3C) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
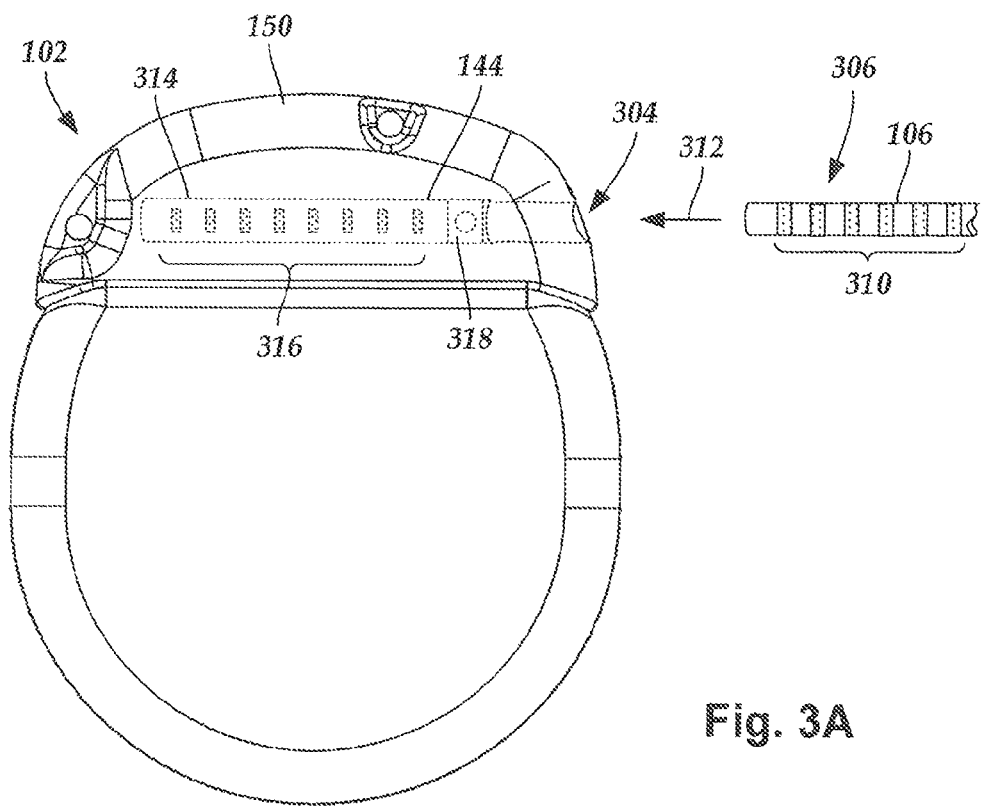
FIG. 3A is a schematic view of one embodiment of a connector assembly disposed in the control module of FIG. 1, the connector assembly configured and arranged to receive the proximal portion of one of the lead bodies of FIG. 1, according to the invention.
Figure 3B:
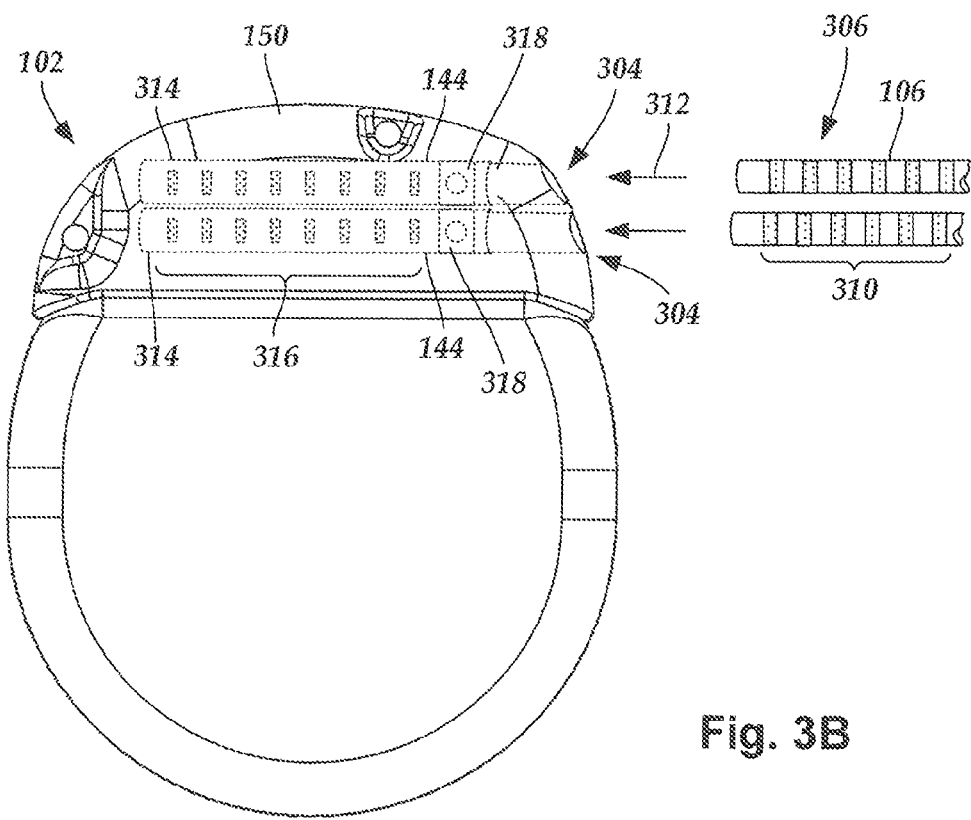
FIG. 3B is a schematic view of one embodiment of a plurality of connector assemblies disposed in the control module of FIG. 1, the connector assemblies configured and arranged to receive the proximal portions of the lead bodies of FIG. 1, according to the invention.

In at least some embodiments, leads are coupled to connectors disposed on control modules. FIG. 3A is a schematic perspective view of one embodiment of a single connector assembly 144 disposed on the control module 102. FIG. 3B is a schematic perspective view of one embodiment of a plurality of connector assemblies 144 disposed on the control module 102. In at least some embodiments, the control module 102 includes two connector assemblies 144. In at least some embodiments, the control module 102 includes four connector assemblies 144. In FIGS. 3A and 3B, the proximal ends 306 of one or more lead bodies 106 are shown configured and arranged for insertion to the control module 102. In FIGS. 3A and 3B, the one or more connector assemblies 144 are disposed in the header 150. In at least some embodiments, the header 150 defines one or more ports 304 into which a proximal end 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 308 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body or lead extension.

When the one or more lead bodies 106 are inserted into the one or more ports 304, the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
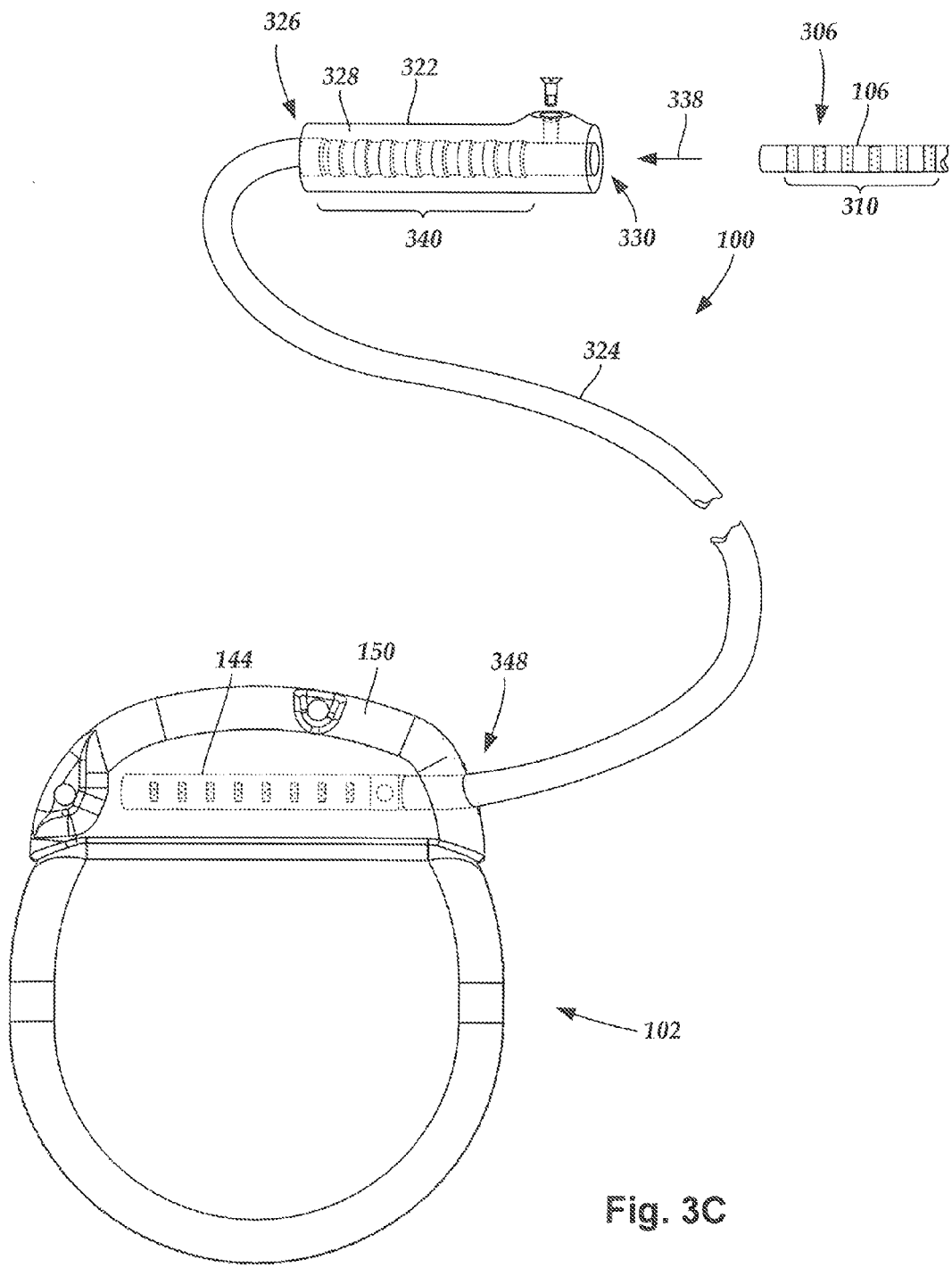
FIG. 3C is a schematic view of one embodiment of a proximal portion of one of the lead bodies of FIG. 1, a lead extension, and the control module of FIG. 1, the lead extension configured and arranged to couple the lead body to the control module, according to the invention.

In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to a proximal end 348 of the lead extension 324 that is opposite to the distal end 326. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102.

Conventional electrical stimulation systems may be potentially unsafe for use with magnetic resonance imaging ("MRI") due to the effects of electromagnetic fields in an MRI environment. A common mechanism for causing the electrical interactions between the electrical stimulation system and RF irradiation is common-mode coupling of the applied electromagnetic fields that act as a series of distributed sources along elongated conductive structures, such as leads, or conductors within leads. Common-mode induced RF currents can reach amplitudes of greater than one ampere in MRI environments. Such currents can cause heating and potentially disruptive voltages within electronic circuits.

Some of the effects of RF irradiation may include, for example, inducing current in the lead, causing undesired heating of the lead that may potentially cause tissue damage, undesired or unexpected operation of electronic components, or premature failure of electronic components. Additionally, when an electrical stimulation system is used within an MRI scanner environment, the electrical interactions between the electrical stimulation system and the MRI may cause distortions in images formed by the MRI system.

Figure 4:
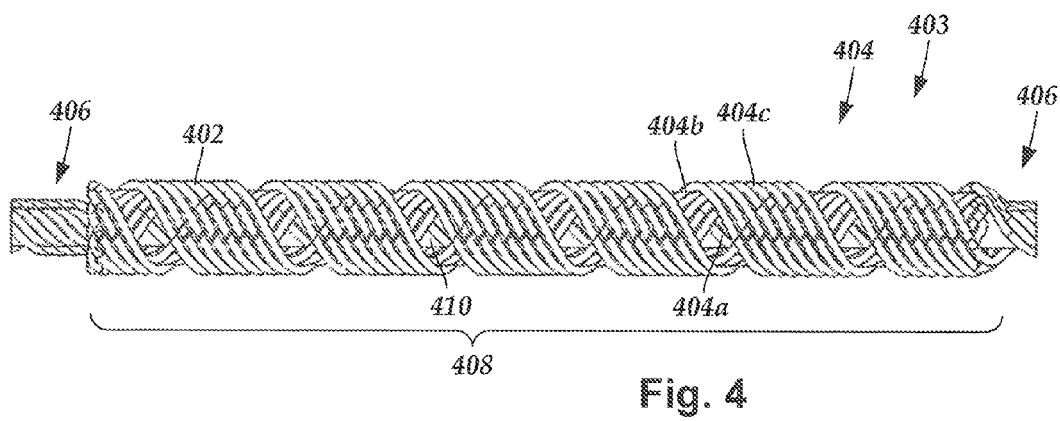
FIG. 4 is a schematic side view of one embodiment of a conductor having a coiled geometry, the coils of the conductor having a constant diameter and pitch along a length of the conductor, according to the invention.

Turning now to FIG. 4, in at least some embodiments the conductors have coiled geometries that include a plurality of common-mode current suppression units ("units") arranged in series. Examples of electrical stimulation systems with leads having conductors formed into units are found in, for example, U.S. Pat. Nos. 8,322,026; 8,335,570; 8,340,782; 8,364,279; 8,380,324; and 8,478,423; and U.S. Patent Application Publications Nos. 2012/0158072 and 2012/0191167, all of which are incorporated by reference.

In at least some embodiments, each unit includes at least three conductor segments that at least partially overlap one another to form a multi-layer region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-layer region flanking at least one end of the multi-layer region.

The units may be electrically continuous such that the endpoint of a first unit is the beginning point of the next consecutive unit. At least one of the beginning points for the series of units may be a terminal or an electrode (or other conductive contact). Likewise, at least one of the endpoints for the series of units may be a terminal or an electrode (or other conductive contact). In preferred embodiments, the conductor segments are each coiled. In at least some embodiments, the conductor segments are coiled around a liner. In at least some embodiments, the liner defines a lumen that optionally is configured and arranged to receive a stiffening member (e.g., a stylet, or the like).

In some embodiments, at least one of the first, second, or third conductor segments is substantially straight. In at least some embodiments, the first and third conductor segments are substantially straight and the second conductor segment is coiled. In some other embodiments, all three conductor segments are substantially straight. It will be understood that the term "substantially straight conductor segment" means that the conductor segment is not coiled. A "substantially straight conductor segment" may be curved (but does not make a full revolution around a circumference of the lead along a length of the conductor segment), particularly when the lead itself is curved (see, for example, FIG. 1).

In some embodiments, the conductor segments are all formed from the same length of conductive material (e.g., wire, or the like). The conductors may have a single filament or be multi-filar, and they may be simple materials or composite constructions, such as drawn filled tubes. In preferred embodiments, the conductors are multi-filar drawn filled tubes. In some embodiments, two or more of the conductor segments can be individual pieces of conductive material that are electrically coupled (e.g., soldered or welded) together.

In some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of conductor insulation disposed around the conductors is different for the different segments.

FIG. 4 schematically illustrates one embodiment of a plurality of conductors 402. The conductors 402 include at least one region 403 that has at least one unit, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-layer regions, such as the single-layer regions 406, separated from one another by a multi-layer region, such as the multi-layer region 408.

Figure 5:
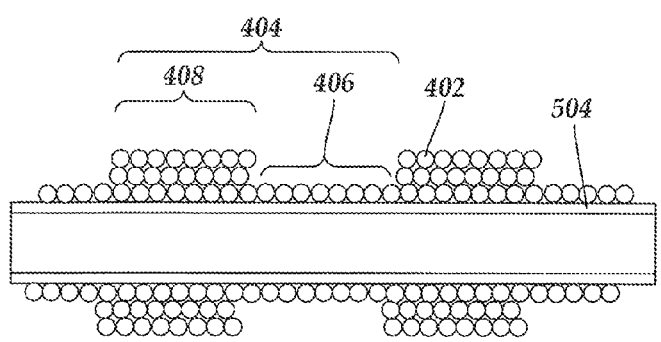
FIG. 5 is a schematic side view of one embodiment of the conductor of FIG. 4 being formed by coiling the conductor along an isodiametric outer surface of a liner disposed over a mandrel, according to the invention.

FIG. 5 is a schematic longitudinal cross-sectional view of one embodiment of portions of the conductors 402 configured into units 404. The conductors 402 are coiled over the constant-diameter liner 504. As shown in FIG. 5, arranging the conductors 402 into units 404 can form a repeating series of single-layer regions 406, separated from one another by multi-layer regions 408. Thus, when the conductors 402 are coiled over the constant diameter liner 504, the multi-layer regions 408 may have outer diameters that are larger than outer diameters of the single-layer regions 406.

Figure 6:
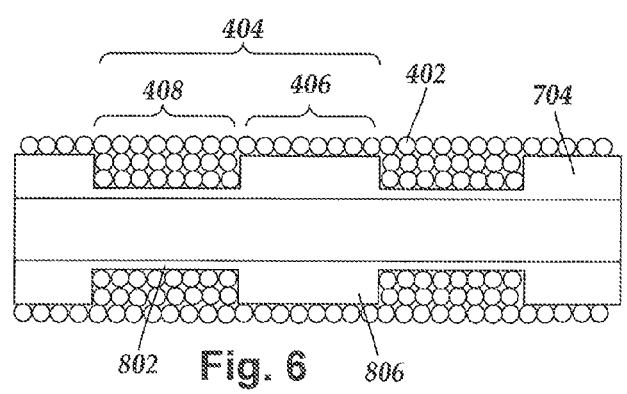
FIG. 6 is a schematic side view of one embodiment of a conductor having a coiled geometry, the coils of the conductor having multiple diameters along a length of the conductor, according to the invention.

In at least some embodiments, conductors 402 can be configured into units 404 using a variable-diameter liner. FIG. 6 is a schematic longitudinal cross-sectional view of one embodiment of portions of the conductors 402 coiled onto the variable-diameter liner 704. In preferred embodiments, the conductors 402 are coiled onto the liner 704 such that one or more of the multi-layer regions 408 of the conductors 402 are aligned with one or more of the first regions 802 of the liner 704, and one or more of the single-layer regions 406 of the conductors 402 are aligned with one or more of the second regions 806 of the liner 704. In at least some embodiments, the difference in diameter between the first region 802 and the second region 806 is equal to the difference in diameter between the single-layer regions 406 and the multi-layer regions 408 of the conductors 402. In which case, the conductors 402 may have a constant outer diameter (e.g., are isodiametric) along the lead.

Figure 7:
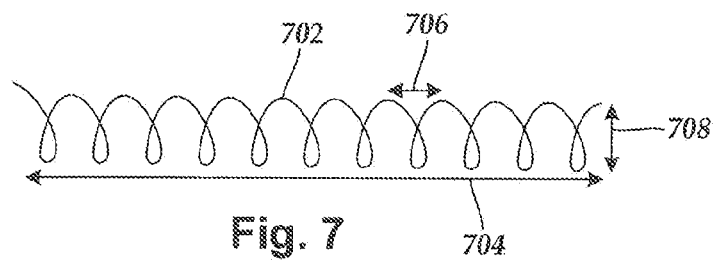
FIG. 7 is a schematic side view of one embodiment of a coiled portion of a conductor, according to the invention.

Alternatively, the conductors can be provided in any other coiled geometry. FIG. 7 is a schematic side view of one embodiment of a conductor 702 having a coiled geometry. The conductor 702 in FIG. 7 has a length 704 and the coils have constant pitch 706 and constant outer diameter 708 along the length 704 of the conductor 702. The conductor 702 can be a single filament or can be multi-filar. In some embodiments, the conductor 702 is formed as separate conductive elements electrically coupled together in series. In many instances, conductor insulation is disposed over the conductors to encapsulate the conductors and electrically isolate the conductors from one another. In FIG. 7, and in other figures, the conductors are shown without being covered in insulation for clarity of illustration.

The conductors 702 can be coiled using any suitable technique. One technique involves winding the conductor 702 around a liner disposed over a mandrel. After the conductors 702 are coiled, the mandrel may be removed. The liner may become a part of the final lead assembly. In some cases, the liner may define a lumen that may be used to receive a stiffening member (e.g., a stylet) for facilitating insertion of the lead into the patient.

Figure 8:
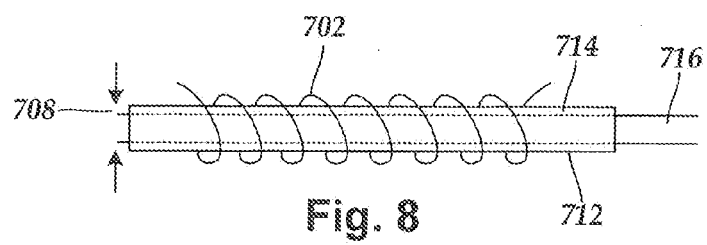
FIG. 8 is a schematic side view of one embodiment of a conductor being formed by coiling the conductor along an outer surface of a liner disposed over a mandrel, the liner having a plurality of different diameters, according to the invention.

FIG. 8 is a schematic side view of one embodiment of the conductor 702 coiled along an outer surface 712 of a liner 714 disposed over a mandrel 716. In this particular embodiment, the outer surface 712 of the liner 714 is isodiametric with a diameter 718, but it will be understood that non-isodiametric liners can also be used. In the illustrated embodiment, when the conductor 702 is coiled around the liner 714, the conductor 702 forms coils having constant diameters 708. In alternate embodiments, the conductor 702 may be coiled around the mandrel 716 without using the liner 714.

The diameter of the coils of the conductor can be different along one or more regions of the conductor. Changing the diameter of the coils along one or more regions of the conductor may alter the electromagnetic properties along all, or a portion, of the lead. Increasing the diameter of the coils may increase the inductance or the capacitance of the coil locally (e.g., in proximity to the individual region of the conductor having coils with an increased diameter). For example, the inductance of a coil may be increased by increasing the cross-sectional area of the coil. Additionally, the capacitance of a coil may be increased by creating a longer total wire length for capacitive coupling. Conversely, decreasing the diameter of the coils may decrease the inductance or the capacitance of the coil locally. These local effects (alone or in combination with altering pitch or the number of filars) may, in turn, affect the global electromagnetic properties of the conductors.

Although the conductors can be coiled along most of the length of the lead, at the proximal and distal ends of the leads, the end of the conductors are not coiled or are slightly coiled (e.g., coiled with a substantially longer pitch than the coiled section or with a substantially smaller coil diameter). Instead, these ends of the conductors are not coiled to allow for attachment to the terminals and electrodes, respectively. The benefits of using a coiled conductor to prevent or reduce induced current in response to RF irradiation are reduced or completely lost at the ends of the conductors because the ends of the conductors are not coiled or are not formed into multilayered coils (see, e.g., multi-layer regions 408 of FIG. 5). In particular, in at least some instances, it has been found that the heating of tissue adjacent to the electrodes of a lead increases from the proximal-most electrode to the distal-most electrode. One possible explanation is that this general trend correlates with the length of the uncoiled distal end of the conductor. The more distal the electrode, the longer the uncoiled, or unprotected, distal end of the conductor (see, FIG. 9).

To reduce the amount of induced current generated in the proximal or distal ends of the conductors (or both ends of the conductors) in response to a RF field, a coiled, internal conductive structure, such as one or more dummy coils, may be provided at the proximal or distal end (or both ends) of the lead. A dummy coil is a coil of wire that is not conductively connected to any of the conductors, electrodes, or terminals and is used herein to illustrate the coiled, internal conductive structure. It will be understood that, even though the dummy coil is not conductively connected to any of the conductors, electrodes, or terminals, the dummy coil may be capacitively or inductively coupled to one or more of the conductors, electrodes, or terminals. As used herein, the term "conductively connected" refers to attachment the two conductively connected components using wires, conductive traces, or other conductive component(s) and does not include capacitive or inductive coupling.

Although not wishing to be bound by any particular theory, the dummy coil may interact with a portion of the applied RF field, thereby reducing or eliminating the amount of current induced by the RF field in the conductors and, in particular, in uncoiled distal or proximal ends of the conductors. Alternatively or additionally, the dummy coil may inductively or capacitively couple to the conductors and, thereby reduce the amount of induced current flowing through the conductors. In at least some embodiments, the dummy coil, or any of the other structures (e.g., conductive structure 1050, conductive structures 1160, or non-therapeutic electrodes 1265) described below, redistributes or more evenly distributes the applied RF field, amount of current induced by the RF field, or heating of tissue by an array of electrodes than would be the case if the dummy coil, or other structure, was absent.

Figure 9:
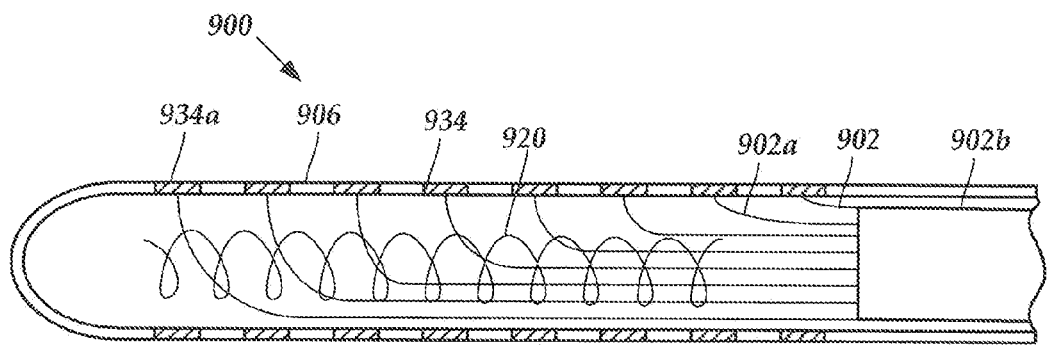
FIG. 9 is a cross-sectional view of one embodiment of a distal or proximal portion of a lead with a dummy coil, according to the invention.

FIG. 9 illustrates one embodiment of a distal or proximal end of a lead 900 having a lead body 906, one or more electrodes (or terminals) 934, and one or more conductors 902 that couple to the electrodes (or terminals) 934. Each of the conductors includes an uncoiled portion 902a and a coiled portion that is collectively represented by box 902b. The uncoiled portion 902a of each conductor 902 extends from one of the electrodes (or terminals) 934 to the coiled portion 902b of the conductor.

The lead 900 further includes at least one dummy coil 920 disposed within the lead near the end of the lead. The dummy coil 920 is not conductively attached to any of the electrodes (or terminals) 934 or conductors 902. The dummy coil may be grounded. For example, the dummy coil 920 may be conductively coupled to tissue (for example, through the distal tip of the lead) or capacitively coupled to tissue at one or more MRI frequencies. Preferably, the dummy coil 920 is covered with insulation. The conductors 902 may go through the dummy coil 920 or around or over the dummy coil or any combination thereof.

Preferably, the dummy coil 920 is disposed near the end-most electrode (or terminal) 934a. The dummy coil 920 may extend along the portion of the lead containing multiple electrodes or terminals, as illustrated in FIG. 9, or only along a portion of the lead containing a single electrode or terminal (for example, the end-most electrode or terminal—the distal-most electrode or the proximal-most terminal). In at least some instances, the distal-most electrode in an arrangement without the dummy coil has the most tissue heating associated with the electrode. Accordingly, placing the dummy coil along at least the portion of the lead containing the distal-most electrode reduces tissue heating associated with that electrode. Therefore, in at least some embodiments, the dummy coil may extend beyond (e.g., proximally) the portion of the lead containing the distal-most electrode or only along the portion of the lead containing the distal-most electrode. In some embodiments, the dummy coil 920 extends along the portion of the lead containing all of the electrodes or all of the terminals. Although the embodiment of FIG. 9 illustrates the use of the dummy coil with conductors having a coiled portion, it will be recognized that the dummy coil 920 can also be used in leads having conductors that do not include a coiled portion.

Optionally, one or more parameters of the dummy coil (e.g., length, diameter, pitch, number of turns) or the positioning of the dummy coil within the lead (or any combination of these factors) may be selected to enhance or increase the reduction of induced current in the conductors 902. For example, in some embodiments, more turns of the coil or tighter coil pitch can produce a higher reduction in induced current. In at least some embodiments, the dummy coil can take the form of a braided structure; optionally, with two or more coils braided together. In other embodiments, the dummy coil may include two or more coils wound in different directions. For example, the dummy coil may include a first section wound in a first direction followed by a second section wound in a second direction, opposite the first direction, followed by a third section wound in the first direction. This dummy coil could be similar in structure to one or more of the units 404 of the conductor 402 illustrated in FIG. 4.

Optionally one of more of these parameters or the positioning of the dummy coil may be selected to enhance coupling of the dummy coil 920 to the RF field, for example, to "tune" the dummy coil to an expected RF frequency. For example, an expected RF frequency may be a typical MRI frequency such as 64 MHz, 85 MHz, or 128 MHz. Optionally, one or more parameters of the dummy coil (e.g., length, diameter, pitch, number of turns) or the positioning of the dummy coil within the lead (or any combination of these factors) may be selected to enhance or increase the impedance of the dummy coil to facilitate dissipation of current induced in the dummy coil.

In at least some embodiments, the dummy coil has a pitch that is equal to a pitch of the coiled portion of at least one of the conductors. In at least some embodiments, the dummy coil has a coil diameter that is equal to a coil diameter of the coiled portion of at least one of the conductors.

In at least some embodiments, to reduce the amount of induced current generated in the proximal or distal ends of the conductors (or both ends of the conductors) in response to a RF field, a non-coiled, internal conductive structure, such as a tube or two or more connected conductive elements, may be placed within the lead under one or more of the electrodes. This conductive structure is not conductively connected to any of the conductors, electrodes, or terminals. It will be understood that, even though the conductive structure is not conductively connected to any of the conductors, electrodes, or terminals, the conductive structure may be capacitively or inductively coupled to one or more of the conductors, electrodes, or terminals.

Although not wishing to be bound by any particular theory, the conductive structure may interact with a portion of the applied RF field, thereby reducing or eliminating the amount of current induced by the RF field in the conductors and, in particular, in uncoiled distal or proximal ends of the conductors. Alternatively or additionally, the conductive structure may inductively or capacitively couple to the conductors and, thereby reduce the amount of induced current flowing through the conductors.

Figure 10:
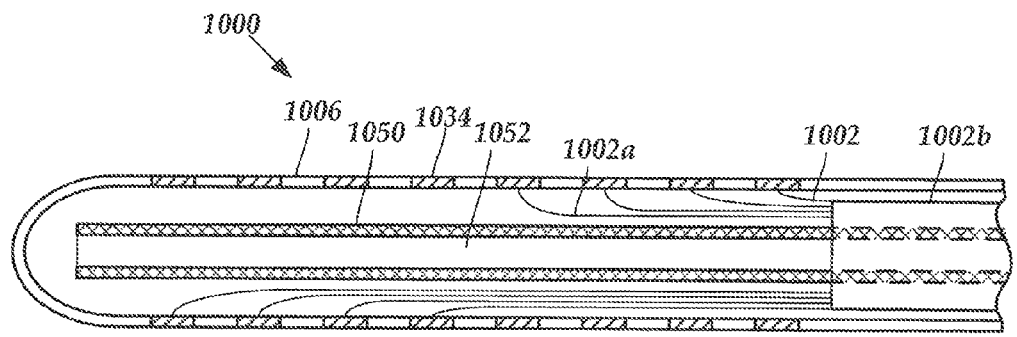
FIG. 10 is a cross-sectional view of one embodiment of a distal or proximal portion of a lead with an internal conductive structure, according to the invention.

FIG. 10 illustrates one embodiment of a distal or proximal end of a lead 1000 having a lead body 1006, one or more electrodes (or terminals) 1034, and one or more conductors 1002 that couple to the electrodes (or terminals) 1034. Each of the conductors includes an uncoiled portion 1002a and a coiled portion that is collectively represented by box 1002b. The uncoiled portion 1002a of each conductor 1002 extends from one of the electrodes (or terminals) 1034 to the coiled portion 1002b of the conductor.

The lead 1000 further includes at least one internal conductive structure 1050, such as a hollow tube (e.g., a hypotube) or solid core, disposed within the lead near the end of the lead. In some embodiments, the conductive structure may define a lumen 1052 that may, for example, provide access for a stylet or guidewire. In some embodiments, the conductive structure may also extend into the coiled portion 1002b of the conductors 1002. The conductive structure 1050 is not conductively attached to any of the electrodes (or terminals) 1034 or conductors 1002. The conductive structure may be grounded. For example, the conductive structure 1050 may be conductively coupled to tissue (for example, through the distal tip of the lead) or capacitively coupled to tissue at one or more MRI frequencies. The conductors 1002 may go through the conductive structure 1050 or around or over the conductive structure or any combination thereof.

Preferably, the conductive structure 1050 is disposed near the end-most electrode (or terminal). The conductive structure 1050 may extend along the portion of the lead containing multiple electrodes or terminals, as illustrated in FIG. 10, or only along a portion of the lead containing a single electrode or terminal (for example, the end-most electrode or terminal—the distal-most electrode or the proximal-most terminal). In some embodiments, the conductive structure 1050 extends along the portion of the lead containing all of the electrodes or all of the terminals. Although the embodiment of FIG. 10 illustrates the use of the conductive structure with conductors having a coiled portion, it will be recognized that the conductive structure 1050 can also be used in leads having conductors that do not include a coiled portion.

The conductive structure 1050 may be made of any suitable conductive material, including, but not limited to, platinum, steel, or Nitinol™. The conductive structure 1050 is preferably formed of a biocompatible material. The conductive structure 1050 may also include an insulation layer disposed over the conductive material.

Figure 11:
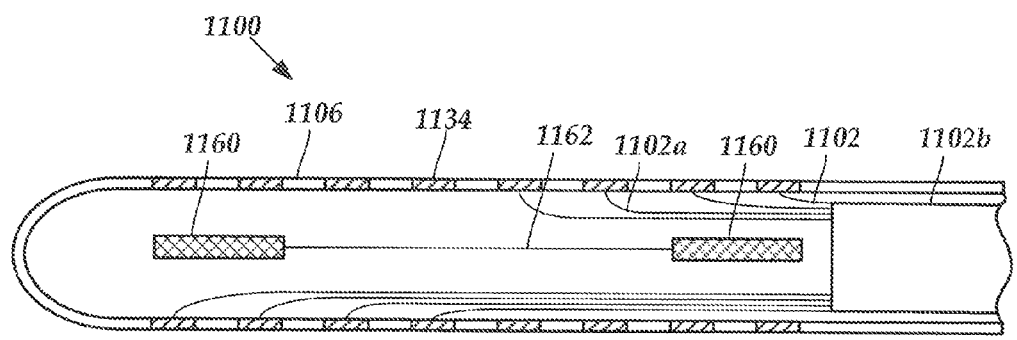
FIG. 11 is a cross-sectional view of one embodiment of a distal or proximal portion of a lead with two conductive structures coupled together by a connection wire, according to the invention.

FIG. 11 illustrates one embodiment of a distal or proximal end of a lead 1100 having a lead body 1106, one or more electrodes (or terminals) 1134, and one or more conductors 1102 that couple to the electrodes (or terminals) 1134. Each of the conductors includes an uncoiled portion 1102a and a coiled portion that is collectively represented by box 1102b. The uncoiled portion 1102a of each conductor 1102 extends from one of the electrodes (or terminals) 1134 to the coiled portion 1102b of the conductor.

The lead 1100 further includes at least two internal conductive structures 1160 disposed within the lead near the end of the lead and connected together by a connection wire 1162. The conductive structures 1160 may be, for example, a rod, tube, or other piece of conductive material. The conductive structures 1160 and connection wire 1162 are not conductively attached to any of the electrodes (or terminals) 1134 or conductors 1102. The conductive structures 1160 and connection wire 1162 may be grounded. For example, the conductive structures 1160 and connection wire 1162 may be conductively coupled to tissue (for example, through the distal tip of the lead) or capacitively coupled to tissue at one or more MRI frequencies.

Preferably, at least one of the conductive structures 1160 is disposed near the end-most electrode (or terminal). The other one of the conductive structures 1160 may be disposed within the same portion of the lead or at any other position within the lead. For example, if one of the conductive structures 1160 is disposed near the end-most electrode along the distal portion of the lead the other conductive structure could be disposed proximal to all of the electrodes or even disposed near the terminals (e.g., 310 in FIGS. 3A-3C) along the proximal portion of the lead.

Each of these conductive structures 1160 (as well as any other conductive structure) may extend along the portion of the lead containing multiple electrodes or terminals, as illustrated in FIG. 11, or only along a portion of the lead containing a single electrode or terminal (for example, the end-most electrode or terminal—the distal-most electrode or the proximal-most terminal). Although the embodiment of FIG. 11 illustrates the use of the conductive structures with conductors having a coiled portion, it will be recognized that the conductive structures 1160 can also be used in leads having conductors that do not include a coiled portion.

The conductive structures 1160 and connector wire 1162 may be made of any suitable conductive material, including, but not limited to, platinum, steel, or Nitinol™. The conductive structures 1160 and connector wire 1162 are preferably formed of a biocompatible material. The conductive structures 1160 and connector wire 1162 may also include an insulation layer disposed over the conductive material.

Figure 12:
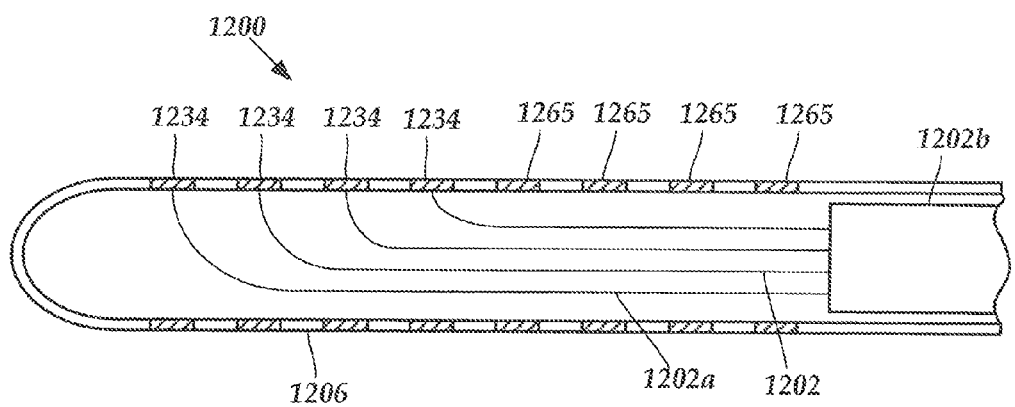
FIG. 12 is a cross-sectional view of one embodiment of a distal or proximal portion of a lead with non-therapeutic electrodes, according to the invention.

In some embodiments, non-therapeutic electrodes can be included in the lead and may divert or otherwise reduce the amount of induced current at the therapeutic electrodes. FIG. 12 illustrates one embodiment of a distal end of a lead 1200 having a lead body 1206, one or more therapeutic electrodes 1234, and one or more conductors 1202 that couple to the therapeutic electrodes 1234. Each of the conductors includes an uncoiled portion 1202a and a coiled portion that is collectively represented by box 1202b. The uncoiled portion 1202a of each conductor 1202 extends from one of the therapeutic electrodes 1234 to the coiled portion 1202b of the conductor.

The lead 1200 further includes one or more non-therapeutic electrodes 1265 disposed within the lead near the distal end of the lead. The one or more non-therapeutic electrodes 1265 may be grounded. The one or more non-therapeutic electrodes 1265 may be disposed proximal to, distal to, or between the therapeutic electrodes 1234.

To reduce the amount of induced current generated in the proximal or distal ends of the conductors (or both ends of the conductors) in response to a RF field, the one or more non-therapeutic electrodes 1265 are provided on the lead with the one or more therapeutic electrodes 1234. The one or more non-therapeutic electrodes 1265 are not conductively connected to any of the conductors 1202, therapeutic electrodes 1234, or terminals. It will be understood that, even though the non-therapeutic electrode is not conductively connected to any of the conductors, therapeutic electrodes, or terminals, the non-therapeutic electrode may be capacitively or inductively coupled to one or more of the conductors, therapeutic electrodes, or terminals.

Although not wishing to be bound by any particular theory, the non-therapeutic electrode may interact with a portion of the applied RF field, thereby reducing or eliminating the amount of current induced by the RF field in the conductors and, in particular, in uncoiled distal ends of the conductors. Alternatively or additionally, the non-therapeutic electrode may inductively or capacitively couple to the conductors and, thereby reduce the amount of induced current flowing through the conductors or dissipate the current generated in the conductors over a wider area (e.g., the combined surface areas of the non-therapeutic and therapeutic electrodes). The non-therapeutic electrodes will typically interact or capacitively/inductively couple less with the conductors when the conductors carry the lower frequency stimulation current than when the conductors carry the higher frequency MRI-induced current.

Figure 13:
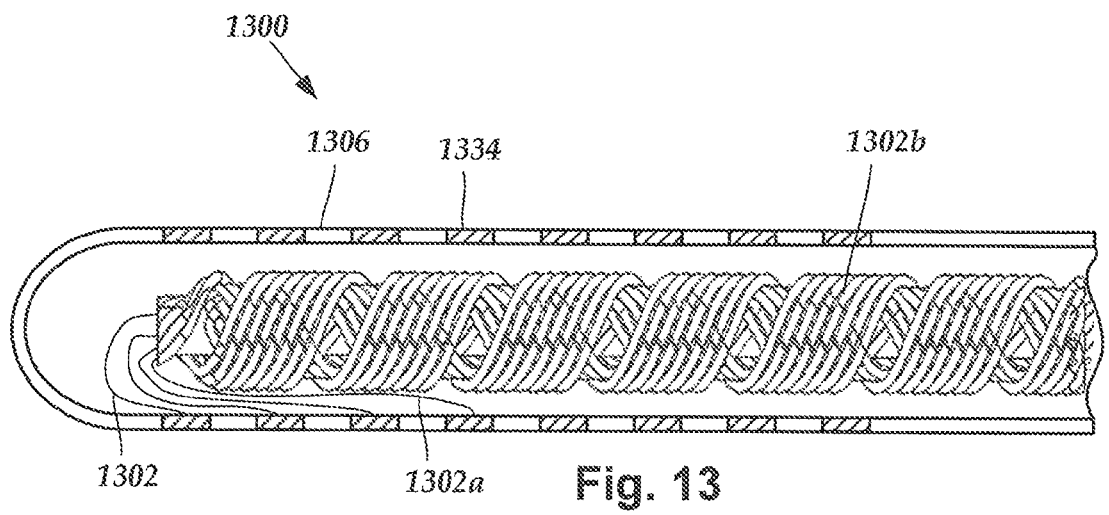
FIG. 13 is a cross-sectional view of one embodiment of a distal or proximal portion of a lead with the coiled conductors disposed beneath the electrodes, according to the invention (for clarity of illustration only four uncoiled portions 1302a of the conductors 1302 (those extending to the four left-most electrodes) are illustrated—it will be understood that other uncoiled portions of conductors extend to each of the four right-most electrodes as well)

In some embodiments, the coiled section of the conductors extends beneath one or more (preferably, all) of the electrodes of the lead. Preferably, the coiled section of the conductors that extends beneath one or more of the electrodes is, or contains, at least one multi-layer region having two or more overlapping conductor segments for each of the conductors, as discussed above. FIG. 13 illustrates one embodiment of a distal end of a lead 1300 having a lead body 1306, one or more electrodes 1334, and one or more conductors 1302 that couple to the electrodes 1334. Each of the conductors 1302 includes an uncoiled portion 1302a and a coiled portion 1302b. For clarity of illustration, the uncoiled portions 1302a of only four of the conductors (those coupled to the four distal-most electrodes 1334) are illustrated in FIG. 13. It will be understood that the other four electrodes are also coupled to the coiled portions 1302b of the conductors by uncoiled portions of the conductors that are not illustrated. The uncoiled portion 1302a of each conductor 1302 extends from one of the electrodes 1334 to the coiled portion 1302b of the conductor. Alternatively, instead of all of the uncoiled portions 1302a extending from the same end of the coiled portions 1302b to the respective electrodes 1334, as illustrated in FIG. 13, each coiled portion 1302b of a respective connector could be interrupted at the longitudinal position of the corresponding electrode in the lead for making direct connection to that electrode.

To reduce the amount of induced current generated in the proximal or distal ends of the conductors (or both ends of the conductors) in response to a RF field, the coiled portions 1302b of the conductors 1302 extend under one or more (preferably, all) of the electrodes (or terminals) 1334. Preferably, the coiled portions 1302b of the conductors that extend beneath one or more of the electrodes 1334 is a multi-layer region containing two or more overlapping conductor segments for one or more (or even each) of the conductors 1302.

Although not wishing to be bound by any particular theory, the coiled portions 1302b (and, in particular, the multi-layer regions) of the conductors 1302 may interact with a portion of the applied RF field, thereby reducing or eliminating the amount of current induced by the RF field in the uncoiled portions 1302a of the conductors or the electrodes 1334.

Figure 14:
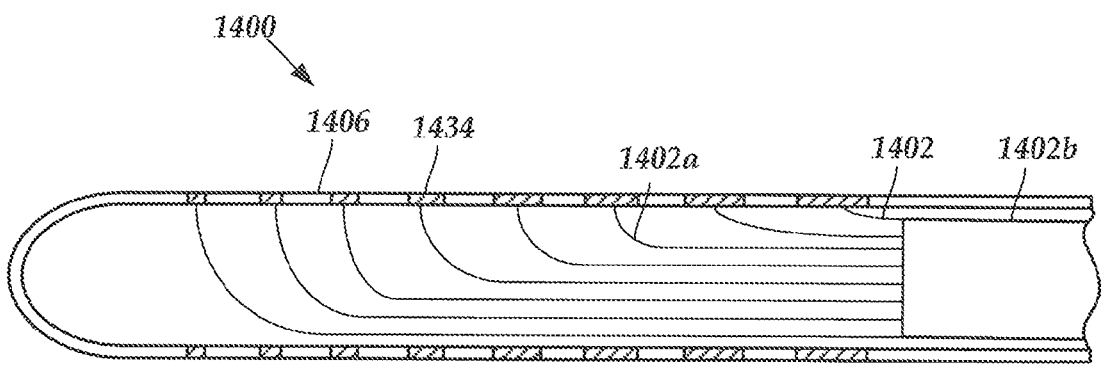
FIG. 14 is a cross-sectional view of one embodiment of a distal or proximal portion of a lead with electrodes that vary in size, according to the invention.

In some embodiments, the energy induced by MRI and dissipated through the electrodes may be modified by modifying the relative shapes of the electrodes. In particular, electrode(s) through which more MRI-induced energy would otherwise be dissipated (e.g., the distal-most electrodes) may have a modified shape to reduce the amount of MRI-induced energy that would be dissipated through those electrode(s) relative to other electrode(s). FIG. 14 illustrates one embodiment of a distal end of a lead 1400 having a lead body 1406, multiple electrodes 1434, and one or more conductors 1402 that couple to the electrodes 1434. Each of the conductors 1402 includes an uncoiled portion 1402a and a coiled portion 1402b.

In the embodiment of FIG. 14, the size and surface area of the electrodes 1434 increases from the distal-most electrode to the proximal-most electrode. This arrangement is particularly useful in leads where, if the electrodes were the same size, each electrode would dissipate less energy than those electrodes distal to it. By varying the size, as illustrated in FIG. 14, the amount of MRI-induced energy dissipated at each electrode can be made more uniform. Alternatively or additionally, one or more of the electrodes 1434 can be dimpled, ridged, or otherwise roughened to increase its effective surface area (as an alternative or in addition to using a larger electrode).

It will be understood that variation of size (or surface texture) can be applied to all of the electrodes or terminals of a lead or to only a subset of the electrodes or terminals of the lead.

It will be understood that any of the embodiments illustrated in FIGS. 9 through 14 can be combined together in any combination to provide further reduction in the induced MRI-current dissipated at one or more of the electrodes. It is contemplated that any combination can include the structures or arrangements illustrated and described for two or more of the embodiments illustrated in FIGS. 9 through 14.

Figure 15:
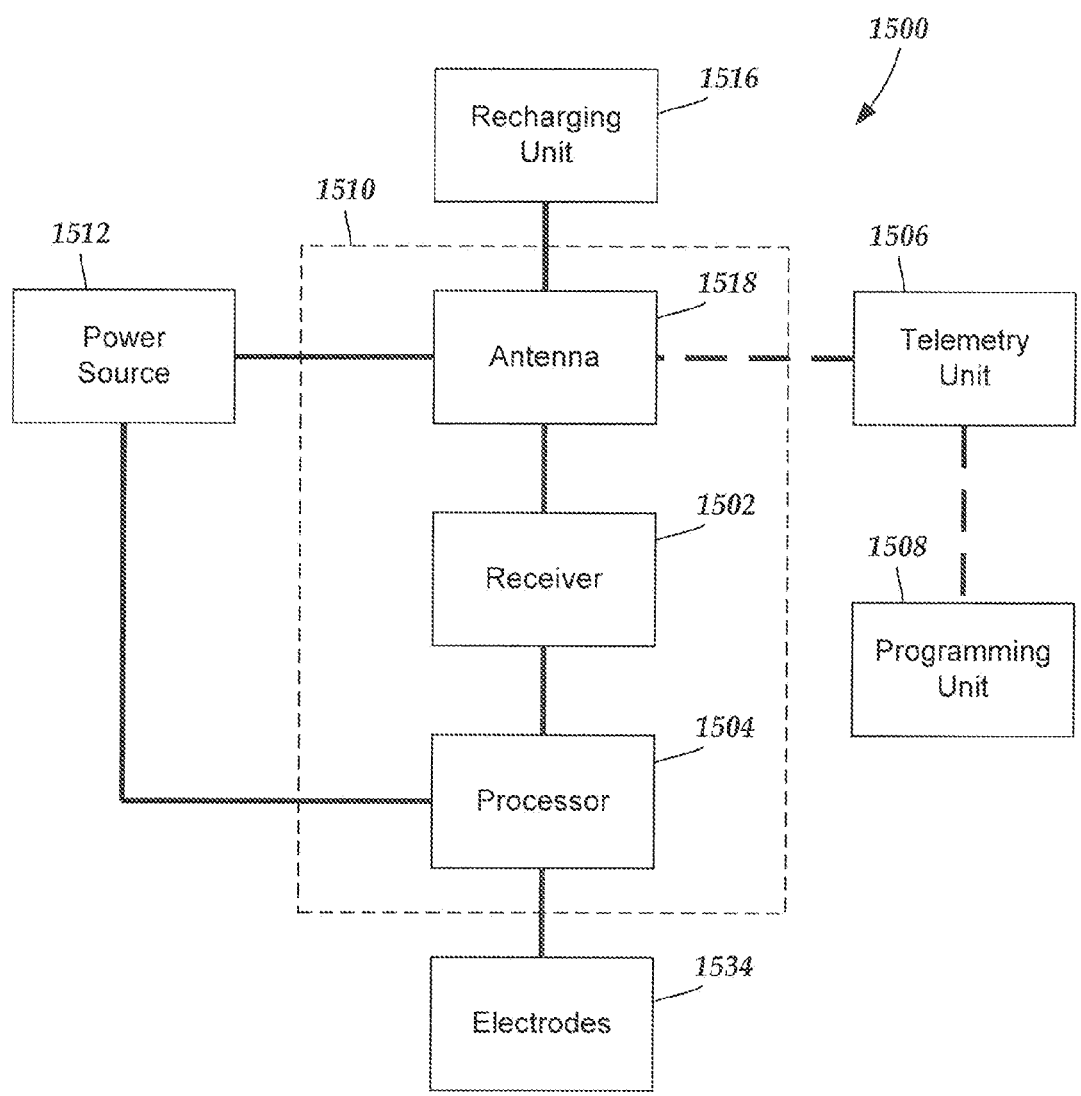
FIG. 15 is a schematic overview of one embodiment of components of a stimulation system, including an electronic subassembly disposed within a control module, according to the invention.

FIG. 15 is a schematic overview of one embodiment of components of an electrical stimulation system 1500 including an electronic subassembly 1510 disposed within a control module. It will be understood that the electrical stimulation system can include more, fewer, or different components and can have a variety of different configurations including those configurations disclosed in the stimulator references cited herein.

Some of the components (for example, power source 1512, antenna 1518, receiver 1502, and processor 1504) of the electrical stimulation system can be positioned on one or more circuit boards or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1518 or a secondary antenna. The external power source can be in a device that is mounted on the skin of the user or in a unit that is provided near the user on a permanent or periodic basis.

If the power source 1512 is a rechargeable battery, the battery may be recharged using the optional antenna 1518, if desired. Power can be provided to the battery for recharging by inductively coupling the battery through the antenna to a recharging unit 1516 external to the user. Examples of such arrangements can be found in the references identified above.

In one embodiment, electrical current is emitted by the electrodes 1534 on the paddle or lead body to stimulate nerve fibers, muscle fibers, or other body tissues near the electrical stimulation system. A processor 1504 is generally included to control the timing and electrical characteristics of the electrical stimulation system. For example, the processor 1504 can, if desired, control one or more of the timing, frequency, strength, duration, and waveform of the pulses. In addition, the processor 1504 can select which electrodes can be used to provide stimulation, if desired. In some embodiments, the processor 1504 may select which electrode(s) are cathodes and which electrode(s) are anodes. In some embodiments, the processor 1504 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1504 is coupled to a receiver 1502 which, in turn, is coupled to the optional antenna 1518. This allows the processor 1504 to receive instructions from an external source to, for example, direct the pulse characteristics and the selection of electrodes, if desired.

In one embodiment, the antenna 1518 is capable of receiving signals (e.g., RF signals) from an external telemetry unit 1506 which is programmed by a programming unit 1508. The programming unit 1508 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 1506 may not be worn or carried by the user but may only be available at a home station or at a clinician's office. The programming unit 1508 can be any unit that can provide information to the telemetry unit 1506 for transmission to the electrical stimulation system 1500. The programming unit 1508 can be part of the telemetry unit 1506 or can provide signals or information to the telemetry unit 1506 via a wireless or wired connection. One example of a suitable programming unit is a computer operated by the user or clinician to send signals to the telemetry unit 1506.

The signals sent to the processor 1504 via the antenna 1518 and receiver 1502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1500 to cease operation, to start operation, to start charging the battery, or to stop charging the battery. In other embodiments, the stimulation system does not include an antenna 1518 or receiver 1502 and the processor 1504 operates as programmed.

Optionally, the electrical stimulation system 1500 may include a transmitter (not shown) coupled to the processor 1504 and the antenna 1518 for transmitting signals back to the telemetry unit 1506 or another unit capable of receiving the signals. For example, the electrical stimulation system 1500 may transmit signals indicating whether the electrical stimulation system 1500 is operating properly or not or indicating when the battery needs to be charged or the level of charge remaining in the battery. The processor 1504 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation lead comprising:
   a lead body having a distal end, a proximal end, and a longitudinal length;
   a plurality of electrodes disposed along the distal end of the lead body;
   a plurality of terminals disposed along the proximal end of the lead body;
   a plurality of conductors electrically coupling the plurality of electrodes to the plurality of terminals; and
   at least one internal conductive structure disposed within the distal end or proximal end of the lead body near at least one of the electrodes or terminals, respectively, wherein the at least one internal conductive structure is not conductively connected to the electrodes, terminals, or conductors, wherein the at least one internal conductive structure comprises a dummy coil disposed within the distal end of the lead body and extending radially under at least a distal-most one of the plurality of electrodes.

2. The lead of claim 1, wherein the dummy coil extends along a portion of the lead containing a plurality of the plurality of electrodes.

3. A method for stimulating tissue, the method comprising:
   implanting the lead of claim 1 into tissue of a patient such that at least some of the electrodes are disposed in proximity to tissue to be stimulated; and
   providing current to at least some of the electrodes from an electrically coupled pulse generator.

4. The lead of claim 1, wherein the dummy coil is grounded.

5. The lead of claim 1, wherein each of the plurality of conductors comprises a coiled portion and an uncoiled distal portion that extends from the coiled portion to a one of the plurality of electrodes to which the conductor is coupled.

6. An electrical stimulation system comprising:
   the lead of claim 1;
   a control module configured and arranged to electrically couple to the proximal end of the lead body, the control module comprising
      a housing, and
      an electronic subassembly disposed in the housing; and
   a connector for receiving the lead, the connector having a proximal end, a distal end, and a longitudinal length, the connector comprising
      a connector housing defining a port at the distal end of the connector, the port configured and arranged for receiving the proximal end of the lead body, and
      a plurality of connector contacts disposed in the connector housing, the connector contacts configured and arranged to couple to at least one of the plurality of terminals disposed on the proximal end of the lead body.

7. The method of claim 3, further comprising applying a RI field to the lead and tissue.

8. The method of claim 7, wherein applying a RF field comprises conducting an MRI procedure on a patient within whom the lead is implanted.

9. The lead of claim 5, wherein the dummy coil has a pitch that is equal to a pitch of the coiled portion of at least one of the conductors.

10. The lead of claim 5, wherein the dummy coil has a coil diameter that is equal to a coil diameter of the coiled portion of at least one of the conductors.

11. The electrical stimulation system of claim 6, further comprising a lead extension configured and arranged to couple the lead to the control module, wherein the connector is disposed on the lead extension.

* * * * *